(12) United States Patent
Venkatraman et al.

(10) Patent No.: US 6,275,728 B1
(45) Date of Patent: Aug. 14, 2001

(54) THIN POLYMER FILM DRUG RESERVOIRS

(75) Inventors: Subramanian S. Venkatraman, Palo Alto; Eli J. Goldman, Menlo Park; Lothar W. Kleiner, Los Altos; Stephanus Pudjijanto, Union City, all of CA (US)

(73) Assignee: ALZA Corporation, Mountain View, CA (US)

( * ) Notice: Subject to any disclaimer, the term of this patent is extended or adjusted under 35 U.S.C. 154(b) by 0 days.

(21) Appl. No.: 09/467,084

(22) Filed: Dec. 10, 1999

Related U.S. Application Data

(60) Provisional application No. 60/113,509, filed on Dec. 22, 1998.

(51) Int. Cl.[7] ...................................................... A61N 1/30
(52) U.S. Cl. ............................................................ 604/20
(58) Field of Search ............................... 604/20, 19, 500, 604/501, 289; 607/149, 150, 151, 152, 153; 206/440; 602/48; 424/424

(56) References Cited

U.S. PATENT DOCUMENTS

| | | | |
|---|---|---|---|
| 3,991,755 | 11/1976 | Vernon et al. | 128/172.1 |
| 4,141,359 | 2/1979 | Jacobsen et al. | 128/172.1 |
| 4,250,878 | 2/1981 | Jacobsen et al. | 128/207.21 |
| 4,383,529 | 5/1983 | Webster | 604/20 |
| 4,398,545 | 8/1983 | Wilson | 128/798 |
| 4,474,570 | 10/1984 | Ariura et al. | 604/20 |
| 4,842,577 | 6/1989 | Konno et al. | 604/20 |
| 4,878,892 | 11/1989 | Sibalis et al. | 604/20 |
| 4,940,456 | 7/1990 | Sibalis et al. | 604/20 |
| 5,087,242 | 2/1992 | Petelenz et al. | 604/20 |
| 5,158,537 | 10/1992 | Haak et al. | 604/20 |
| 5,310,404 | 5/1994 | Gyory et al. | 604/20 |
| 5,328,455 | 7/1994 | Llyod et al. | 604/20 |
| 5,385,543 | 1/1995 | Haak et al. | 604/20 |
| 5,533,972 | 7/1996 | Gyory et al. | 604/20 |

FOREIGN PATENT DOCUMENTS

| | | | |
|---|---|---|---|
| 410 009 | 5/1934 | (DE) . | |
| WO 92/07619 | 5/1992 | (WO) | A61N/1/30 |
| WO 92/20324 | 11/1992 | (WO) | A61K/9/14 |
| WO 93/24177 | 12/1993 | (WO) | A61N/1/30 |

OTHER PUBLICATIONS

Rein, Hermann, "Experimental Investigation of Electro–Endosmosis in Living Humn Skin", Zeitschrift fur Biologies, vol. 81, Munich, 1924, pp 126–140. English translation, pp 1–28 also attached.

*Primary Examiner*—Manuel Mendez
(74) *Attorney, Agent, or Firm*—Owen J. Bates; Steven F. Stone

(57) ABSTRACT

The present invention relates to hydratable drug reservoir films for electrotransport drug delivery devices and to electrotransport drug delivery systems containing the hydratable drug reservoirs and to methods for manufacturing and using such systems. The hydratable reservoir films according to this invention are easily manufacturable and rapidly imbibe water and/or drug solution with good water retention and stability.

28 Claims, 1 Drawing Sheet

| TIME, HOURS | LHRH FLUX | FENTANYL FLUX |
|---|---|---|
| 0 | 0 | 0 |
| 1.5 | 0 | 36.64 |
| 3.5 | 3.62 | 59.38 |
| 5.5 | 13.7 | 69.73 |
| 7.5 | 24.41 | 76.76 |
| 9.5 | 29.76 | 83 |

| TIME, HOURS | LHRH FLUX | FENTANYL FLUX |
|---|---|---|
| 0 | 0 | 0 |
| 1.5 | 0 | 36.64 |
| 3.5 | 3.62 | 59.38 |
| 5.5 | 13.7 | 69.73 |
| 7.5 | 24.41 | 76.76 |
| 9.5 | 29.76 | 83 |

THIN POLYMER FILM DRUG RESERVOIRS

CROSS-REFERENCE TO RELATED APPLICATIONS

The application claims priority from U.S. provisional application Ser. No. 60/113,509, filed on Dec. 22, 1998.

TECHNICAL FIELD

The present invention relates to transdermal drug delivery. More particularly and without limitation, the present invention relates to thin film, anhydrous, hydratable drug reservoir materials useful as a drug reservoir material for transdermal drug delivery devices. The present invention relates to transdermal drug delivery systems containing the hydratable drug reservoirs and to methods for manufacturing and using such systems.

BACKGROUND OF THE INVENTION

Iontophoresis, according to Dorland's Illustrated Medical Dictionary, is defined to be "the introduction, by means of electric current, of ions of soluble salts into the tissues of the body for therapeutic purposes." Iontophoretic devices have been known since the early 1900's. British patent specification No. 410,009 (1934) describes an iontophoretic device which overcame one of the disadvantages of such early devices known to the art at that time, namely the requirement of a special low tension (low voltage) source of current which meant that the patient needed to be immobilized near such source. The device of the British patent specification was made by forming a galvanic cell from the electrodes and the material containing the medicament or drug to be delivered transdermally. The galvanic cell produced the current necessary for iontophoretically delivering the medicament. This ambulatory device thus permitted iontophoretic drug delivery with substantially less interference with the patient's daily activity.

More recently, a number of United States patents have issued in the electrolytic transdermal delivery field, indicating a renewed interest in this mode of drug delivery. For example, U.S. Pat. No. 3,991,755 issued to Vernon et al., U.S. Pat. No. 4,141,359 issued to Jacobsen et al., U.S. Pat. No. 4,398,545 issued to Wilson, and U.S. Pat. No. 4,250,878 issued to Jacobsen disclose examples of iontophoretic devices and some applications thereof. The iontophoresis process has been found to be useful in the transdermal administration of medicaments or drugs including lidocaine hydrochloride, hydrocortisone, fluoride, penicillin, dexamethasone sodium phosphate, insulin and many other drugs. Perhaps the most common use of iontophoresis is in diagnosing cystic fibrosis by delivering pilocarpine salts iontophoretically. The pilocarpine stimulates sweat production; the sweat is then collected and analyzed for its chloride content to detect the presence of the disease.

In presently known iontophoretic devices, at least two electrodes are used. Both of these electrodes are disposed so as to be in intimate electrical contact with some portion of the skin of the body. One electrode, called the active or donor electrode, is the electrode from which the ionic substance, medicament, drug precursor or drug is delivered into the body by iontophoresis. The other electrode, called the counter or return electrode, serves to close the electrical circuit through the body. In conjunction with the patient's skin contacted by the electrodes, the circuit is completed by connection of the electrodes to a source of electrical energy, e.g., a battery. For example, if the ionic substance to be delivered into the body is positively charged (i.e., a cation), then the anode will be the active electrode and the cathode will serve to complete the circuit. If the ionic substance to be delivered is negatively charged (i.e. an anion), then the cathode will be the active electrode and the anode will be the counter electrode.

Alternatively, both the anode and cathode may be used to deliver drugs of opposite charge into the body. In such a case, both electrodes are considered to be active or donor electrodes. For example, the anode can deliver a positively charged ionic substance into the body while the cathode can deliver a negatively charged ionic substance into the body.

It is also known that iontophoretic delivery devices can be used to deliver an uncharged drug or agent into the body. This is accomplished by a process called electroosmosis. Transdermal delivery of neutral compounds by the phenomenon of electroosmosis is described by Hermann Rein in Zeitschrift fur Biologie, Bd. 8 1, pp 125–140 (1924) and the transdermal delivery of non-ionic polypeptides by the phenomenon of electroosmosis is described in Sibalis et al., U.S. Pat. Nos. 4,878,892 and 4,940,456. Electroosmosis is the transdermal flux of a liquid solvent (e.g., the liquid solvent containing the uncharged drug or agent) which is induced by the presence of an electric field imposed across the skin by the donor electrode. Similarly, electrophoresis is the transdermal flux of both the solute and the liquid solvent in an electric field. As used herein, the terms "electrotransport" and "electrolytic transdermal delivery" encompass both the delivery of charged ions as well as the delivery of uncharged molecules by the associated phenomenons of iontophoresis, electroosmosis, and electrophoresis.

Electrotransport delivery devices generally require a reservoir or source of the beneficial agent (which is preferably an ionized or ionizable agent or a precursor of such agent) to be iontophoretically delivered or introduced into the body. Examples of such reservoirs or sources of ionized or ionizable agents include a pouch or cavity as described in the previously mentioned Jacobsen, U.S. Pat. No. 4,250,878, a porous sponge or pad as disclosed in Jacobsen et al., U.S. Pat. No. 4,141,359, or a preformed gel body as described in Webster, U.S. Pat. No. 4,383,529, and Ariura et al., U.S. Pat. No. 4,474,570. Such drug reservoirs are electrically connected to the anode or the cathode of an electrotransport device to provide a fixed or renewable source of one or more desired agents.

Electrotransport delivery devices which are attachable at a skin surface and rely on electrolyte fluids to establish electrical contact with such skin surfaces can be divided into at least two categories. The first category includes those devices which are prepackaged with the liquid electrolyte contained in the electrode receptacle. The second type of device uses dry-state electrodes whose receptacles or reservoirs are customarily filled with liquid drug/electrolyte immediately prior to application to the body. With both types of devices, the user currently experiences numerous problems which make their use both inconvenient and problematic.

With respect to the prefilled device, storage is a major concern. Many drugs have poor stability when in solution. Accordingly, the shelf life of prefilled iontophoretic drug delivery devices with such drug solutions is unacceptably short. Corrosion of the electrodes and other electrical components is also a potential problem with prefilled devices. For example, the return electrode assembly will usually contain an electrolyte salt such as sodium chloride which over time can cause corrosion of metallic and other electrically conductive materials in the electrode assembly. Leakage is another serious problem with prefilled iontophoretic drug delivery devices. Leakage of drug or electrolyte from the electrode receptacle can result in an inoperative or defective state. Furthermore, such prefilled devices are difficult to apply because the protective seal which covers the electrode opening and retains the fluid within the receptacle cavity must be removed prior to application on the skin. After removal of this protective seal, spillage often occurs in attempting to place the electrode on the skin. Such spillage impairs the desired adhesive contact of the electrode to the skin and also voids a portion of the receptacle cavity. The consequent loss of drug or electrolyte fluid tends to disrupt electrical contact with the electrode plate contained therein and otherwise disrupts the preferred uniform potential gradient to be applied.

Although dry-state electrodes have numerous advantages in ease of storage, several problems remain. For example, the drug and electrolyte receptacles of such a device are conventionally filled through an opening prior to application of the device to the patient's skin. Therefore, the same problem of spillage and loss of drug or electrolyte upon application occurs as with the pre-filled electrode.

Frequently, such electrodes are not well structured to develop the proper uniform current flow required in iontophoresis applications. Such nonuniform current flow may result from the occurrence of air pockets within the receptacle cavity at the skin surface. Such effects are particularly troublesome in electrolytic transdermal delivery applications, where a nonuniform current distribution may result in excessive skin irritation or "burning".

Hydrogels have been particularly favored for use as the drug reservoir matrix and electrolyte reservoir matrix in electrotransport delivery devices, in part due to their high equilibrium water content and their ability to absorb water from the body. In addition, hydrogels tend to have good biocompatibility with the skin and with mucosal membranes. However, since many drugs and certain electrode components are unstable in the presence of water, electrotransport drug delivery devices having a drug reservoir formed of a prehydrated hydrogel may also have unacceptably short shelf life. In particular, certain therapeutic agents have a limited shelf life at ambient temperature in an aqueous environment. Notable examples are insulin and prostaglandin sodium salt ($PGE_1$).

One proposed solution to the drug stability problem is to use hydrophilic polymer drug and electrolyte reservoirs which are in a substantially dry or anhydrous state, i.e. in a non-hydrated condition. The drug and/or electrolyte can be dry blended with the hydrophilic polymer and then cast or extruded to form a non-hydrated, though hydratable, drug or electrolyte containing reservoir. Alternative methods also involve the evaporation of water and/or solvent from solution or emulsion polymers to form a dry polymer film. This process is energy intensive, however, and requires a large capital investment for equipment.

In addition, the prior art non-hydrated hydrophilic polymer components must first absorb sufficient quantities of water from the body before the device can operate to deliver a drug. This delay makes many devices unsuited for their intended purpose. For example, when using an iontophoretic delivery device to apply a local anesthetic in preparation for a minor surgery (e.g. surgical removal of a mole), the surgeon and the patient must wait until the drug and electrolyte reservoirs of the delivery device become sufficiently hydrated before the anesthetic is delivered in sufficient quantities to induce anesthesia. Similar delays are encountered with other drugs.

In response to these difficulties, Konno et al., in U.S. Pat. No. 4,842,577, disclose in FIG. 4 an electrotransport device having a substantially non-hydrated drug containing layer or membrane filter and a separate water reservoir which is initially sealed, using a foil sheet, from the drug containing portions of the electrode. Unfortunately, this electrode design is not only difficult to manufacture but also is subject to severe handling restriction. In particular, there is a tendency for the foil seal to be inadvertently broken during manufacture, packaging, and handling of the electrode. This can have particularly drastic consequences especially when the seal is broken during manufacture of the device. Once the seal is broken, water is wicked into the drug-containing reservoir which can cause degradation of the drug and/or other components before the device is ever used.

Hydratable iontophoretic devices are known in the electrotransport art as disclosed in U.S. Pat. Nos. 5,158,537, 5,310,404, and 5,385,543, which are hereby incorporated in their entirety by reference. The reservoirs of these devices are preferably composed, at least in part, of a hydrophilic, natural or synthetic polymer material. Reservoir materials including low-substituted hydroxy propyl cellulose and hydrogels such as polyhydroxyethyl methacrylate are disclosed. The reservoir matrix may also include a hydrophobic polymer such as polyurethanes in order to enhance lamination of the reservoir to adjacent layers. Preferred hydroxypropyl cellulose and hydrophilic polyurethane compositions are not disclosed.

Additionally, WO 92/20324 discloses polyurethane hydrogel compositions for iontophoretic drug delivery. These polyurethane hydrogel compositions are prepared by dissolving an isocyanate-capped oxyalkylene-based polymer in a first solvent which comprises an anhydrous aprotic organic solvent to give a prepolymer solution. The prepolymer solution is then mixed with a second solvent which comprises water and optionally a water-miscible organic solvent to give a hydrogel forming mixture, which is then allowed to cure to give a hydrogel matrix. The hydrogels may alternately be prepared by mixing the isocyanate-capped oxyalkylene-based prepolymer in a total solvent comprising water and a water-miscible organic solvent to give the hydrogel forming mixture. Additional hydratable drug reservoirs for iontophoretic drug delivery devices are disclosed in U.S. Pat. Nos. 5,087,242 and 5,328,455, which are hereby incorporated in their entirety by reference.

The hydrophilic polymer components of the hydratable reservoir materials of the prior art typically require an extensive cure step to process the polymers which typically involves high temperatures. Heat sensitive drugs and/or excipients can not be processed at such high temperatures without degradation. Furthermore, such processing requires additional dispensing, casting and/or curing equipment.

Another disadvantage of using non-hydrated hydrophilic polymer components is that they have a tendency to delaminate from other parts of the electrode assembly during hydration. For example, when utilizing a drug reservoir matrix or an electrolyte reservoir matrix composed of a hydrophilic polymer, the matrix begins to swell as it absorbs water from the skin. In the case of hydrogels, the swelling is quite pronounced. Typically, the drug or electrolyte reservoir is in either direct contact, or contact through a thin layer of an ionically conductive adhesive, with an electrode. Typically, the electrode is composed of metal (e.g., a metal foil or a thin layer of metal deposited on a backing layer) or a hydrophobic polymer containing a conductive filler (e.g., a hydrophobic polymer loaded with carbon fibers and/or metal particles). Unlike the hydrophilic drug and electrolyte reservoirs, the electrodes do not absorb water and do not swell. The different swelling properties of the hydrophilic reservoirs and the electrodes results in shearing along their contact surfaces. In severe cases, the shearing can result in the complete loss of electrical contact between the electrode and the drug/electrolyte reservoir resulting in an inoperable device.

Thus, there remains a need for an easily manufacturable, anhydrous drug reservoir with an extended shelf life that can be manufactured at lower temperatures and which rapidly imbibes water and/or drug solution with good water retention and stability.

SUMMARY OF THE INVENTION

Accordingly, it is an aspect of the present invention to provide an electrotransport drug delivery device with drug containing electrode components which are manufactured in an initially free non-hydrated condition but which can be quickly hydrated during processing with stable drugs or hydrated by the end-user with unstable drugs prior to placement on the body.

It is another aspect of this invention to provide a hydratable drug reservoir material for an electrotransport device that can be processed at temperatures sufficient for melt-mixing heat sensitive drugs and/or excipients without causing degradation thereof.

It is another aspect of this invention to provide drug reservoir films for electrotransport drug delivery devices that are flexible and conformable to skin or other body tissue in order to make intimate contact therewith.

It is yet another aspect of this invention to provide hydratable drug reservoir films for electrotransport drug delivery devices which overcome the problems associated with the prior art hydratable drug reservoirs.

These and other aspects of the present invention will be apparent from the drawings and detailed description that follows.

BRIEF DESCRIPTION OF THE DRAWINGS

The objects and advantages of the present invention will become apparent from the following detailed description of the preferred embodiments thereof in connection with the accompanying drawings in which like numerals designate like elements and in which.

DETAILED DESCRIPTION OF THE INVENTION

Figure 1:
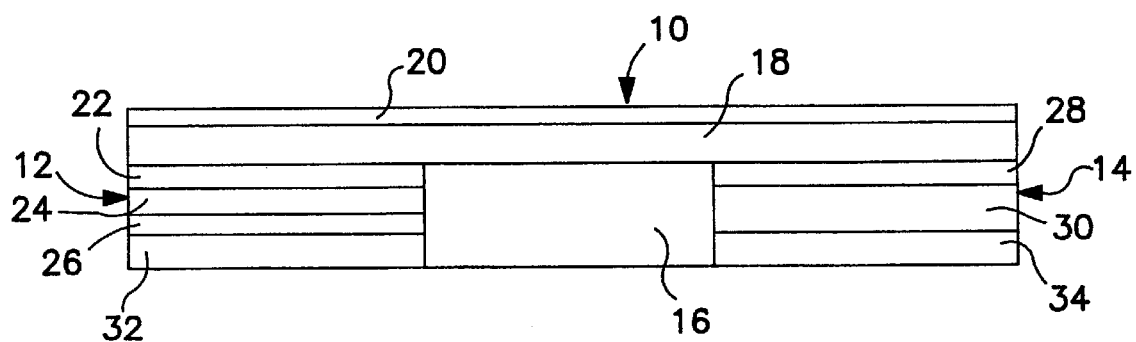
FIG. 1 is a schematic side view of an exemplary electrotransport drug delivery device according to the present invention.

According to the present invention, hydratable films are provided which are particularly well suited as the drug reservoir for an electrotransport drug delivery device. The films of the invention are flexible and conformable and quickly imbibe a hydrating liquid and/or drug solution. The films can retain drug solution for periods of up to 2 years without syneresis and loss of stability. Drug solution can be imbibed into the film during processing and the resulting gel or swollen film used as a drug reservoir in an electrotransport device, or the drug can be incorporated into the film as a solid or liquid component during processing then made part of the electrotransport device in which the end-user imbibes a calculated amount of water or water-excipient mixture to form the drug reservoir just prior to activation. According to another embodiment, devices are manufactured without any drug solution, which is then imbibed into the drug reservoir just prior to use.

With reference to the drawings, electrotransport delivery device 10 includes a donor electrode assembly 12 and a counter electrode assembly 14. The donor electrode assembly 12 and the counter electrode assembly 14 are physically attached to an insulator 16 and form a single self-contained unit. Insulator 16 prevents the electrode assemblies 12 and 14 from short circuiting the body by preventing electrical and/or ion transport between the electrode assemblies 12 and 14. Electrode assemblies 12 and 14 are connected in series, by appropriate electrical conductors as known in the art such as metal foils, wires, printed circuits, or electrically conductive films (not shown), with an electrical power source. The power source and the electrical conductors are schematically shown as layer 18. The power source used to power device 10 is typically one or more low voltage batteries. A water impermeable backing layer 20 may preferably cover layer 18 with its associated electrical components.

The donor electrode assembly 12 typically includes an electrode layer 22 and a reservoir layer 24 containing the beneficial agent to be iontophoretically delivered by device 10. A rate controlling membrane layer 26 may optionally be positioned between the reservoir layer 24 and the body surface for preventing the delivery of agent to the body surface when the device is turned off. Counter electrode assembly 14 contacts the body surface at a location spaced apart from electrode assembly 12. Counter electrode assembly 14 includes an electrode layer 28 and a reservoir layer 30. Device 10 may be adhered to the body surface by means of ion-conducting adhesive layers 32, 34. As an alternative to the ion-conducting adhesive layers 32, 34 shown in FIG. 1, device 10 may be adhered to the body surface using an adhesive overlay. Any of the conventional adhesive overlays used to secure passive transdermal delivery devices to the skin may be used in the present invention.

When used in connection with the reservoir 24 or the electrode assembly 12, the term "agent" refers to beneficial agents, such as drugs, within the class which can be delivered through body surfaces. The expression "drug" is intended to have a broad interpretation as any therapeutically active substance which is delivered to a living organism to produce a desired, usually beneficial effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodiloators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers.

The present electrotransport delivery system is particularly useful in the controlled delivery of peptides, polypeptides, proteins, macromolecules and other drugs which have a tendency to be unstable, hydrolyzed, oxidized, denatured or otherwise degraded in the presence of the liquid, such as water, which is necessary to conduct iontophoresis. For example, drugs containing either an ester bond (i.e., steroids) or an amide bond (i.e., peptides) may be hydrolyzed in water. Specific examples of drugs which can become degraded in the presence of water include catechols, such as apomorphine and epinephrine, salbutamol, sulfhydryls such as captopril, niphedipine and peptides such as VIP and insulin. Examples of other peptides and proteins which may be delivered using the device of the present invention are set forth with particularity in U.S. Pat. No. 5,158,537 issued to Haak et al., and assigned to the present assignee, the entire contents of which are hereby incorporated by reference. Preferred agents for electrotransport delivery according to this invention include fentanyl, LHRH and analogs thereof, and insulin.

When the device 10 is in storage, no current flows because the device does not form a closed circuit. When the device is activated and placed on the skin or mucosal membrane of a patient and the electrode assemblies 12 and 14 are sufficiently hydrated to allow ions to flow through the various layers of the electrode assemblies, the circuit between the electrodes is closed and the power source begins to deliver current through the device and through the body of the patient. The donor and counter electrode assemblies 12 and 14 normally include a strippable release liner (not shown) which is removed prior to application of the electrode assemblies to the body surface. In certain instances, it may also be desirable for the delivery of the beneficial agent through the device 10 to be controlled by the user through a user-actuated switch (not shown).

In accordance with the present invention, the donor reservoir 24 is an anhydrous hydrophilic polymer film containing a therapeutic agent. The reservoir is maintained in a dry state for storage, and then hydrated when ready for use. Hydration of the hydrophilic reservoir film may occur in any known manner, as described in further detail below and as described in the above-cited patents.

The films according to this invention are thin, flexible, and conformable to provide intimate contact with a body surface, are capable of rapid hydration and also are able to release an agent from the reservoir at rates sufficient to achieve therapeutically effective transdermal fluxes of agent. The compositional ranges of the polymers used to make the films of this invention enable this unexpected combination of properties.

The films of this invention are manufactured from hydrophilic base polymers and optional excipients such as hygroscopic additives to improve the kinetics of drug solution and/or water absorption, and/or plasticizers to aid in melt processing as well as rendering the film more flexible after being imbibed with the drug solution. The films do not need to be cross-linked although cross-linking is possible. The hydratable reservoir films according to this invention must absorb at least 1.5 times, preferably about 4–25 times their weight in water while maintaining their mechanical properties.

According to a particularly preferred embodiment, the films comprise a shear modulus, $G'$ (0.1 Hz), within the range of about 1–100 kPa, preferably 1–20 kPa, when at about 400% hydration in order to provide desired flexibility and conformability. The films according to this embodiment are capable of absorbing about 400–800% of their weight in water, preferably about 500–700%, within about 30 minutes, preferably within about 20 minutes, and most preferably within about 1 minute. Preferably, the base polymer for the films are hydrophilic polyurethanes or hydroxypropyl cellulose (HPC). Most preferably, the films are polyurethane films based on diisocyanate/polyglycol and glycol linkages wherein the glycol is polyethylene glycol.

No additives are necessary for the preferred polyurethane films in order to attain the desired rate of absorption and flexibility. Preferred polyurethane films according to this invention are polyurethanes made by reacting polyethylene glycol with diisocyanates and butanediol and include Tecogel® polyurethanes manufactured by Thermedics of Woburn, Mass., such as Tecogel-500 and Tecogel-2000 series. The relative amount of polyethylene glycol to the other components is adjusted to between 60–95%, preferably about 70–90% of the total weight of the dry matrix. According to another embodiment, a blend of polyethylene oxide and polyethylene glycol with the polyurethane is used in the same ratios.

Other hydrophilic polymers, such as polypropylene oxide and polyethylene oxide, either singly or in any possible combination with polyethylene glycol, can be used in place of the polyethylene glycol alone, when synthesizing the polyurethane.

For the HPC films of this invention, additives are necessary to render the HPC film flexible and absorbent. Preferably, the hydratable HPC films according to this invention comprise (by weight %) 50–90% HPC such as Klucel® HF grade from Aqualon, 10–30% silica gel or Sephadex®, and 5–30% plasticizer, such as glycerin, propylene glycol, or polyethylene glycol, for example.

According to another preferred embodiment, at least one scrim layer comprised of a hydrophilic material is added to at least one surface of the hydratable film layer. According to this embodiment, a scrim layer may be placed on either surface of the hydratable film layer, or interposed between two hydratable film layers. Alternately, multiple repeating layers of hydratable film and scrim layers may be used according to this embodiment such as to form, for example, an assembly comprising hydratable film/scrim/hydratable film/scrim/hydratable film. The reservoir assemblies according to this embodiment provide additional mechanical integrity and/or increased hydration rates. Additionally, the scrim layer provides a surface which may be laminated to an electrode. According to this embodiment, the water absorption kinetics can be increased to less than a few minutes, preferably less than 1 minute. The scrim is a hydrophilic material including, but not limited to, non-woven cloths or fabric materials such as Rayon®, Rayon®/Polyester blends, or polyvinyl alcohol foams.

The present invention is also directed to methods for manufacturing devices comprising the drug reservoir films according to this invention. According to one embodiment, drug solution can be imbibed into the film during processing. The formation of the hydrophilic therapeutic drug/polymer reservoir films in accordance with this embodiment of the present invention includes the dissolution of the therapeutic agent in aqueous media or a water/organic solvent mixture in order to obtain a low viscosity solution. A suitable solvent would include water, ethanol, isopropanol or a combination of water and an organic solvent. The drug solution may be prepared at ambient or less than ambient temperature for thermally sensitive molecules. In addition, the drug solutions may be mixed with relatively low shear mixing equipment which substantially prevents degradation of shear sensitive molecules.

Once prepared, the solution of the therapeutic agent is applied to the surface of a selected hydrophilic polymer film. Hydrophilic within the terms of the present invention includes all polymers having a liquid absorption rate of generally 1–10 µl/cm$^2$/sec or greater. The film would be unwound from a roll and die-cut into the appropriate size and shape. Drug solution would then be dispensed onto the film on-line. After a suitable time period for absorption of the drug solution into the film (maximum of 10–20 minutes), the film would be covered with a liner and then proceed to the next step. No end-user intervention is required.

According to another embodiment, drug is incorporated into the film as a solid and/or liquid component during processing and subsequently made part of an electrotransport device. The end-user then imbibes a preselected amount of water or water/excipient mixture to hydrate the film just prior to use. According to this embodiment, agent is first dispersed and/or dissolved in the drug reservoir material by mixing and thereafter the film is extruded. In this embodiment, the manufacturer or end-user then adds sufficient water (or other suitable hydrating liquid) to make a swollen drug/polymer mixture for intimate contact to the skin. Alternatively, the end-user can incorporate drug solution in place of the hydrating liquid, in which case the device is provided initially free of agent. Other sources of a hydrating material could of course also be used in the present invention, such as, for example, a liquid pouch as described in U.S. Pat. No. 5,158,537 or a liquid passageway as described in U.S. Pat. No. 5,385,543, the contents of both of which are hereby incorporated by reference.

The solution may be applied to the hydrophilic polymer film using a variety of techniques including spraying, BioDot or any other type of micrometer dispensing, dipping, volumetric metering, or other suitable coating technology. Low viscosity liquids, such as the therapeutic agent solution, are easily and reproducibly dispensed with a volumetric metering pump.

The overall size of the anhydrous films will of course vary dependent upon the therapeutic agent and the amount thereof contained therein, but generally, anhydrous films on the order of 1 to 12 cm$^2$ will be cut for placement into the appropriate reservoirs of the electrotransport system.

Thus, the preparation of the therapeutic agent/hydrophilic polymer film affords a dry polymer matrix which enhances the storage stability of drug molecules that do not possess long term stability in an aqueous environment. In the anhydrous state, the polymer matrix has an extended shelf life and is not subject to the disadvantages and problems encountered with the storage of water sensitive therapeutic agents.

The therapeutic agent/hydrophilic membrane of the present invention is very thin, generally on the order of two to sixty mils, (50.8 microns to 1524 microns), more preferably 6 to 30 mils (152.4 microns to 762 microns). The rate of hydration obtained in the present invention is therefore rapid. Thus, the electrotransport of the therapeutic agent is not delayed as in the prior art devices. The hydrated membrane also remains firmly adhered to the hydrogel, which is partially due to the dimensional stability of the hydrated film. According to the embodiments wherein a scrim layer is used, the combined thickness of the hydratable film layer(s) and scrim layer is about 2–60 mils (50.8 microns to 1524 microns), preferably 6–30 mils (152.4 microns to 762 microns).

EXAMPLE 1

In vitro studies were conducted in 2 compartment electrotransport cells. Each cell consisted of a donor housing thick enough to contain the swollen hydrogel and a 450 µl receptor compartment fitted with circular polypropylene grid to prevent bowing of the skin into the receptor compartment. The anode electrode was silver foil, and the cathode electrode was silver chloride/PIB composite. To determine if holes or tears were present in the human cadaver epidermis, an initial sample was collected after an equilibration time without applied current and analyzed by HPLC. A cell was designated a leaker if drug was present in the passive time point receptor sample. The flow rate of receptor buffer was 250 µl/hr, and vials collecting the receptor solution (1:10 dilution of Dulbeco's phosphate saline buffer) were changed every 1.92 hours by a fraction which was maintained at 4° C.

$^{5}/_{16}$" diameter discs of hydrogel (Tecogel 1000S, Thermedics, Woburn Mass.) at a thickness of 20 mils (508 mcirons) were die-cut and weighed. The discs were then placed in the donor housing and hydrated with 2.5 times their weight in drug solution. The LHRH drug solution had a concentration of 15 mM. The fentanyl solutions were made with sufficient fentanyl HCl to yield a final drug concentration in the hydrogel of 2 wt %. After sitting 10 minutes, a PET liner was applied to the housing to prevent further evaporation. The discs were allowed to hydrate approximately 30 minutes before conducting the flux tests.

Since LHRH and fentanyl are positively charged in the pH range studied (pH 5–8 for LHRH, pH 4–6.5 for fentanyl), only anodic drive experiments were performed; i.e. electrical current was applied such that the donor was anodically polarized with respect to the receptor. All studies were performed at 32° C. maintained by aluminum heat blocks and controllers with at least three replications per condition. Each cell was connected in series to a constant current source set to obtain a current density of 100 µA/cm$^2$, and the voltage drop across the cell was measured and recorded every 20 minutes.

Figure 2:
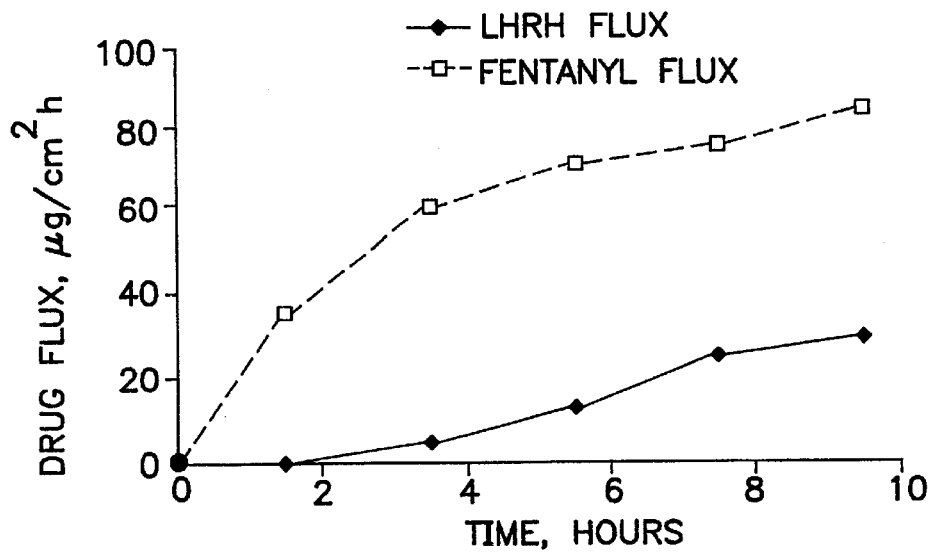
FIG. 2 is a plot depicting flux of LHRH and fentanyl from films according to this invention.

The flux results for LHRH and fentanyl are shown in FIG. 2.

While the invention has been described in detail with reference to the preferred embodiments thereof, it will be apparent to one skilled in the art that various changes and modifications can be made and equivalents employed, without departing from the present invention.

What is claimed is:

1. A thin film drug reservoir for an electrotransport drug delivery device comprising a hydratable, hydrophilic polymer, said film capable of forming a hydrogel when placed in contact with a hydrating liquid, said film, when hydrated at about 400%, having a shear modulus G' of about 1–100 kPa and wherein said film when substantially non-hydrated, is capable of absorbing at least about four times its weight in hydrating liquid within about 30 minutes.

2. A film according to claim 1 wherein said film absorbs about 4 times to about 25 times its weight of hydrating liquid in about 20 minutes.

3. A film according to claim 1 wherein said polymer comprises hydroxypropyl cellulose.

4. A film according to claim 3 wherein said film comprises 5–30 wt % plasticizer, 10–30 wt % hygroscopic additive, and 50–90 wt % hydroxypropyl cellulose.

5. A film according to claim 4 wherein said hygroscopic additive comprises silica gel.

6. A film according to claim 4 wherein said plasticizer comprises at least one compound selected from the group consisting of propylene glycol, polyethylene glycol, and glycerol.

7. A film according to claim 1 wherein said polymer comprises polyurethane.

8. A film according to claim 7 wherein about 60 wt % to about 95 wt % of the covalent structure of the polyurethane polymer is derived from polyethylene glycol.

9. A film according to claim 8 wherein about 80 wt % to about 90 wt % of the covalent structure of the polyurethane polymer is derived from polyethylene glycol.

10. A film according to claim 1 wherein said hydrated shear modulus is about 1 kPa to about 20 kPa.

11. A film according to claim 1 wherein the thickness of said film is between about 50.8 microns and about 1524 microns.

12. A film according to claim 11 wherein the thickness of said film is between about 152.4 microns and about 762 microns.

13. A multilaminate dry state electrode assembly for an electrolytic transdermal agent delivery device, said electrode assembly comprising:
 a reservoir layer including a substantially non-hydrated hydratable matrix containing an agent to be delivered, the reservoir layer being adapted to be placed in agent transmitting relation with a body surface, and
 an electrode layer in electrical contact with both the reservoir layer and a power source,
 wherein said hydratable matrix comprises a hydratable, hydrophilic polymer film, said film capable of forming a hydrogel when placed in contact with a hydrating liquid, said film, when hydrated to about 400%, having a hydrated shear modulus G' of about 1–100 kPa and wherein said film, when substantially non-hydrated, is capable of absorbing at least about four times its weight in hydrating liquid within about 30 minutes.

14. An electrode assembly according to claim 13 wherein said film absorbs about 4 time to about 25 times its weight in hydrating liquid within about 20 minutes.

15. An electrode assembly according to claim 13 wherein said polymer comprises hydroxypropyl cellulose.

16. An electrode assembly according to claim 15 wherein said film comprises 5–30 wt % plasticizer, 10–30 wt % hygroscopic additive, and 50–90 wt % hydroxypropyl cellulose.

17. An electrode assembly according to claim 16 wherein said hygroscopic additive comprises silica gel.

18. An electrode assembly according to claim 16 wherein said plasticizer comprises at least one compound selected from the group consisting of propylene glycol, polyethylene glycol and glycerol.

19. An electrode assembly according to claim 13 wherein said polymer comprises polyurethane.

20. An electrode assembly film according to claim 19 wherein about 60 wt % to about 95 wt % of the covalent structure of the polyurethane is derived from polyethylene glycol.

21. An electrode assembly according to claim 20 wherein about 80 wt % to about 90 wt % of the covalent structure of the polyurethane is derived from polyethylene glycol.

22. An electrode assembly according to claim 13 wherein said shear modulus G' is between about 1 kPa and about 20 kPa.

23. An electrode assembly according to claim 13 wherein the thickness of said film is between about 50.8 microns and about 1524 microns.

24. An electrode assembly according to claim 23 wherein the thickness of said film is between about 152.4 microns and about 762 microns.

25. An electrode assembly according to claim 13 further comprising a second hydratable matrix and a scrim layer positioned between the two hydratable matrices.

26. An electrode assembly according to claim 25 further comprising at least one pair of a hydratable matrix and a scrim layer wherein said scrim layer is positioned between two hydratable matrices.

27. An electrode assembly according to claim 25 wherein each hydratable matrix is made from substantially the same material.

28. An electrode assembly according to claim 26 wherein each hydratable matrix is made from substantially the same material.

* * * * *